United States Patent [19]

Ljungstroem

[11] Patent Number: 5,423,864
[45] Date of Patent: Jun. 13, 1995

[54] DIFIBRILLATION SYSTEM

[75] Inventor: Jan Ljungstroem, Solna, Sweden

[73] Assignee: Siemens Elema AB, Solna, Sweden

[21] Appl. No.: 160,653

[22] Filed: Dec. 2, 1993

[30] Foreign Application Priority Data

Dec. 11, 1992 [SE] Sweden .............................. 92037340

[51] Int. Cl.⁶ .............................................. A61N 1/39
[52] U.S. Cl. ...................................... 607/5; 607/122; 128/642
[58] Field of Search ................... 128/642; 607/5, 115, 607/116, 122, 123, 125–127

[56] References Cited

U.S. PATENT DOCUMENTS

| | | | |
|---|---|---|---|
| 3,326,207 | 6/1967 | Egan | 128/642 |
| 3,937,225 | 2/1976 | Schramm . | |
| 4,662,377 | 5/1987 | Heilman et al. . | |
| 5,010,894 | 4/1991 | Edhag . | |
| 5,170,802 | 12/1992 | Mehra | 607/126 |
| 5,255,678 | 10/1993 | Deslauriers et al. | 128/642 |

FOREIGN PATENT DOCUMENTS

| | | | |
|---|---|---|---|
| 0500289 | 8/1992 | European Pat. Off. . | |
| 0563614 | 10/1993 | European Pat. Off. | 607/126 |
| 2163055 | 2/1986 | United Kingdom | 128/642 |
| 8906148 | 7/1989 | WIPO | 607/126 |

Primary Examiner—Lee S. Cohen
Assistant Examiner—Jeffrey R. Jastrzab
Attorney, Agent, or Firm—Hill, Steadman & Simpson

[57] ABSTRACT

A defibrillation system includes circuitry and other components contained in a defibrillator housing, to which at least two defibrillation electrodes are connected, at least one defibrillation electrode being intended for intracardiac placement. This defibrillation electrode contains a flexible electrode cable with at least one elongate, electrically insulated conductor and at least one defibrillation surface disposed at the distal end of the electrode cable for delivering defibrillation pulses to the heart. The system further includes control components and circuitry for determining when defibrillation therapy, in the form of one or more pulses is to be administered. In order to provide defibrillation employing the intracardiac electrode, with a defibrillation surface that is relatively large so that the defibrillation current can be distributed so as to prevent damage to the heart, while still achieving optimum defibrillation, and so that the defibrillation electrode does not impede the flow of blood in the heart during periods when it is not used to emit pulses, the electrode head is constructed so as to be expandable, and the defibrillator housing includes control elements and circuitry operable on the electrode head via the electrode cable to cause the electrode head to expand, as needed, and to subsequently return to a non-expanded state.

11 Claims, 3 Drawing Sheets

DIFIBRILLATION SYSTEM

BACKGROUND OF THE INVENTION

1. Field of the Invention

The present invention relates to a defibrillation system of the type employing a defibrillator housing to which at least two defibrillation electrodes are connected, with at least one of these electrodes being intended for intracardiac placement.

2. Description of the Prior Art

Defibrillation systems of the type generally described above are known wherein the intracardiac electrode includes a flexible electrode cable with at least one elongate, electrically insulated conductor and at least one defibrillation surface disposed at a distal end of the electrode cable for delivering defibrillation pulses to the heart. Such known systems include control means for determining when defibrillation therapy, in the form of one or more defibrillation pulses, is to be administered via the intracardiac electrode and the other electrodes.

Such a defibrillation system is disclosed in U.S. Pat. No. 4,662,377. This system includes two defibrillation electrodes, one of which is subcutaneous and the other of which is intracardiac Both electrodes are connected to the defibrillator housing. The electrode head of the intracardiac electrode is a helical conductor, having a diameter roughly corresponding to the external diameter of the electrode cable. This conductor extends along a substantial portion of the distal end of the electrode. A disadvantage of such a defibrillation electrode is that it has a defibrillation area which is relatively small, compared to the magnitude of the current which is applied to this area during the delivery of a defibrillation pulse. This can result in damage to the heart due to burning, since the defibrillation surface often presses against the heart wall. As a result of the size, location and concentration of the defibrillation area at one site in the heart, optimum defibrillation is not achieved.

A defibrillation electrode is disclosed in U.S. Pat. No. 5,010,894 intended for intracardiac placement. The electrode head of this known defibrillation electrode is formed by a plurality of outwardly-projecting, pre-curved flexible conductors, which serve as defibrillation surfaces. The proximal ends of the conductors are anchored in adjacent manner in a common connection device at the same time as their distal ends are adjacently anchored to a second common connection device. Before an electrode cable is introduced into a heart via a vein, the electrode head is stretched using a stylet so that the conductors are brought close to each other, thereby giving the electrode head a diameter which is only slightly larger than the diameter of the electrode cable. After the electrode head has been advanced into the heart, the stylet can be withdrawn, thereby permitting the conductors to expand laterally so as to resiliently press against the surrounding wall along a substantial portion of their length. Current applied through this defibrillation electrode can be evenly distributed to these conductors, which jointly form a relatively large defibrillation area. This can prevent burn damage to the surrounding heart wall. Optimum defibrillation can be achieved, because the conductors can be evenly distributed inside the heart. Because the electrode head is permanently lodged in the heart, at least the conductors can be made of a material having excellent properties for permitting the conductors to follow the movements of the heart for a very long period of time without damage to the conductors themselves, or to the heart. Such a relatively large electrode head, however, can impede the flow of blood in the heart.

SUMMARY OF THE INVENTION

It is an object of the present invention to provide a defibrillation system which employs an intracardiac defibrillation electrode having a defibrillation surface which is relatively large, but which is arranged in the heart such that damage to the heart is prevented while still achieving optimum defibrillation.

It is a further object of the present invention to provide such a defibrillation electrode which does not significantly impede the flow of blood in the heart during periods in which it does not needed for emitting stimulation pulses.

The above object is achieved in accordance with the principles of the present invention in a defibrillation system having an intracardiac defibrillation electrode with an electrode head which is expandable, the defibrillation electrode being connected to a defibrillator housing which contains control means, operating through the electrode cable, to cause the electrode head to expand as needed. When the control means senses conditions within the heart indicating a need for defibrillation, the electrode head is expanded by the control means, so that the defibrillation surface thereof presses against the heart walls, so as to deliver stimulation pulses to the heart. When the heart subsequently returns to normal operation, the control means causes the electrode head to resume its original, non-expanded position. In this non-expanded position, the electrode head has a shape which does not impede the flow of blood in the heart. When the electrode head is in this passive position, neither the electrode head nor the surrounding heart wall can be damaged. The shape of the electrode head in the passive position resembles a tubular body forming a longitudinal continuation of the electrode cable, and disposed at approximately the center of one of ventricles.

As used herein, the term defibrillation surface means the totality of the surface area of the electrode head which is used to administer defibrillation therapy to the heart. This term, therefore, encompasses a single surface, or a plurality of electrically interconnected surfaces.

In a further embodiment of the invention, the electrode head of the defibrillation electrode is formed by elastic, inflatable material. The control means includes means for inflating and deflating the electrode head. A substantial portion of the electrode head, when inflated, presses against a large part of the surrounding heart wall.

In a further version of this embodiment of the invention, the defibrillation surface on the inflatable material of the electrode head is formed by filamentous conductors arranged so as to permit the electrode head to expand. The conductors are preferably evenly distributed on the electrode head. A defibrillation surface of a desired size can be achieved by selecting the number and size of the conductors.

In a preferred embodiment of the defibrillation electrode, the electrode head is formed by at least two elongate, flexible, legs which serve in whole or in part as defibrillation surfaces, and which are attached at one end to the electrode cable and which are connected to each other at the opposite ends. The legs are expandable by one or more separation elements disposed between the legs, and operated by the control means. Each of the legs can be provided with a relatively large defibrillation surface. Moreover, the electrode head, depending on the length and number of the legs, can press against most of the surrounding heart wall in the ventricle during defibrillation.

The separation element can be an inflatable, balloon-like component, connected to the electrode cable and disposed between the legs.

In a version of the invention which is simple to construct, the control means is a pump which pumps a gas or liquid through a channel in the electrode cable to and from the electrode head and the electrode head itself, if it consists of elastic material, or to the separation element.

Preferably, the control means acts on the electrode head so that the electrode head expands before a defibrillation pulse is emitted. This ensures optimum defibrillation of the heart.

DESCRIPTION OF THE PREFERRED EMBODIMENTS

Figure 1:
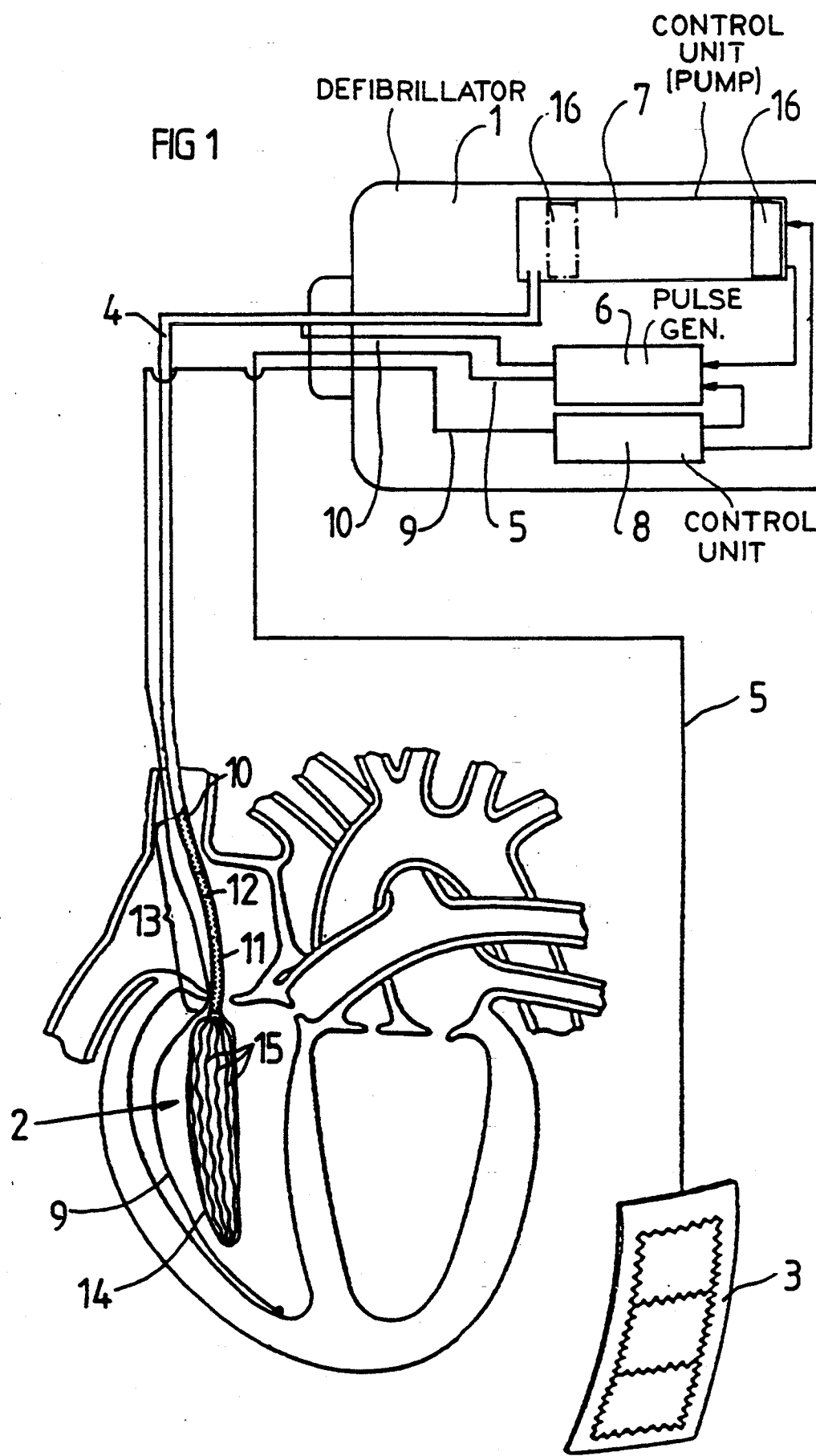
FIG. 1 is a schematic illustration of a first embodiment of a defibrillation system with an intracardiac defibrillation electrode, constructed in accordance with the principles of the present invention, with the electrode head being in an unexpanded state.

A defibrillation system constructed in accordance with the principles of the present invention is shown in FIG. 1 which includes a defibrillator 1 to which two defibrillation electrodes 2 and 3 are connected. As used herein, the term "defibrillator" will refer to the implantable housing and the components contained therein. At least one of the defibrillation electrodes, in this case the defibrillation electrode 2, is intended for intracardiac placement. The other defibrillation electrode, such as the defibrillation electrode 3, can be sited, for example, subcutaneously. The second defibrillation electrode 3, or a third defibrillation electrode (not shown) can be arranged in the region of the superior vena cava, in which case the second defibrillation electrode 3, or the third defibrillation electrode, will have a shape adapted in a known manner to this region. The defibrillation electrodes 2 and 3 are connected via respective electrode cables 4 and 5 to a pulse generator 6 contained within the defibrillator 1. The intracardiac defibrillation electrode 2 is also connected to a control unit 7 in the defibrillator 1. The defibrillation system also includes a control unit 8 to which an intracardiac sensor electrode 9 is connected. The pulse generator 6 and the control units 7 and 8 will be described in greater detail below with reference to FIG. 1 and with reference to FIG. 5.

The intracardiac defibrillation electrode 2 is formed by the aforementioned flexible electrode cable 4, which contains an elongate conductor 10 having an exterior provided with a layer of insulation 11, and having an interior forming a channel 12. This embodiment is illustrated by representation of the longitudinal cross-section 13 of the electrode cable 4. An electrode head 14 is disposed at a distal end of the electrode cable 4. The electrode head 14 is formed by an inflatable material, which is preferably elastic. Defibrillation surfaces are provided on the inflatable material, consisting of filamentous conductors 15 arranged on inflatable material so that they allow the electrode head 14 to expand. In the embodiment of FIG. 1, the conductors 15 are connected to the conductor 10 and run from the point at which the electrode head 14 is attached to the electrode cable 4 to the distal end of the electrode head 14. The conductors 15 are interconnected at the distal end of the electrode head 14 in order to prevent voltage gradients for arising.

Figure 2:
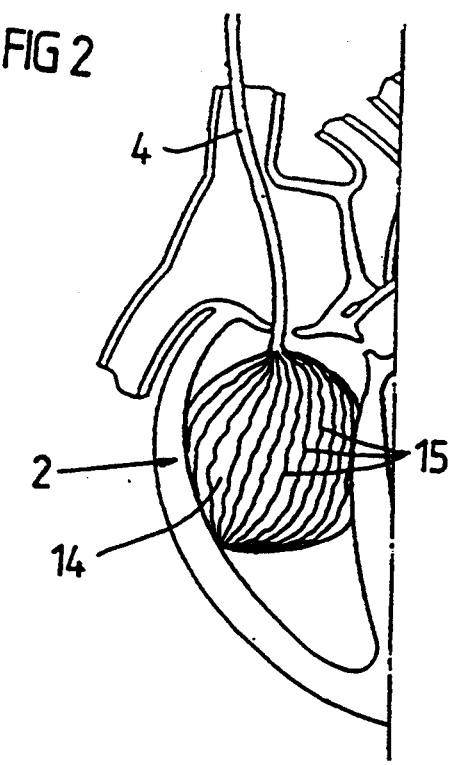
FIG. 2 shows the defibrillation system of FIG. 1 with the electrode head in an expanded state.

When the control unit 8, receiving signals from the sensor electrode 9, identifies conditions indicating the presence of cardiac fibrillation, this information is provided to the control unit 7 which immediately expands the electrode head 14, via the electrode cable 4, so that the outer wall of the electrode head 14 with the filamentous conductors 15 presses tightly against the surrounding wall of the heart, as illustrated in FIG. 2. When the control unit 7 has caused the electrode head 14 to assume this active position, this information is supplied to the pulse generator 6, which is then enabled to emit defibrillation pulses to the heart through the defibrillation electrodes 2 and 3. The control unit 7 for the intracardiac defibrillation electrode 2 is a pump, for example, a reciprocating pump, which pumps a gas or a liquid, such as a saline solution, through the channel 12 of electrode cable 4 to the electrode head 14. The pump 7 is schematically shown in FIG. 1, and provides a representation that a piston 16 in the pump 7 is in the position shown with solid lines when the electrode head 14 is collapsed as shown in FIG. 1. The space in the pump and the channel 12 of the electrode cable 4 is then full of a gas or liquid. Just before cardiac defibrillation begins, the piston 16 is moved to the position shown by the dot-dashed lines, forcing the gas or liquid into the electrode head 14 and causing it to expand in the manner shown in FIG. 2. When the sensor electrode 9 subsequently senses normal cardiac activity, this information is supplied to the control unit 8, which in turn supplies the information to the pulse generator 6, which terminates emission of defibrillation pulses. The information is also supplied to the pump 7, which is operated so as to move the piston 16 in an opposite direction so as to evacuate the gas or fluid from the electrode head 14, causing the electrode head 14 to collapse into its original, passive position shown in FIG. 1.

Figure 3:
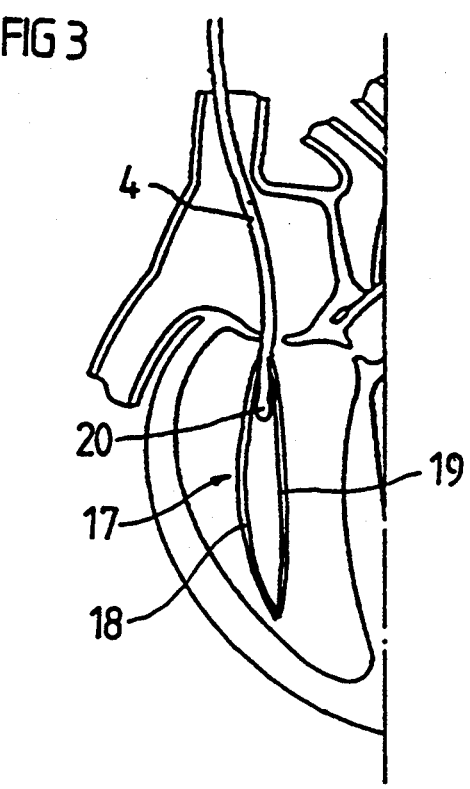
FIGS. 3 and 4 respectively show further embodiments of an intracardiac defibrillation electrode for use in the defibrillation system constructed in accordance with the principles of the present invention.
Figure 4:
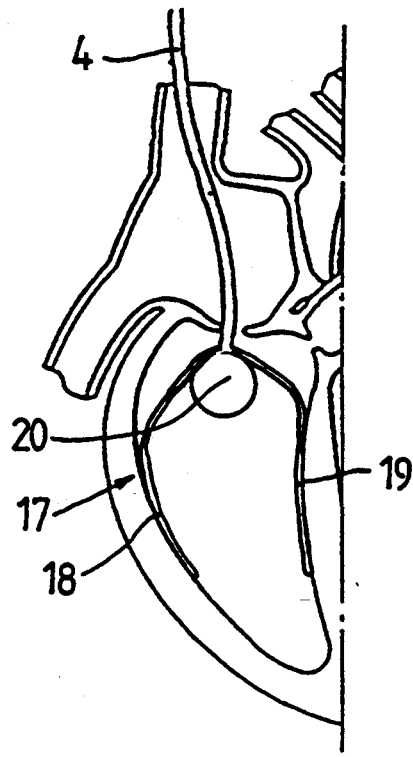

An intracardiac defibrillation electrode with an electrode head 17 is shown in FIG. 3. The embodiment shown in FIG. 3 differs from that shown in FIGS. 1 and 2 in that the electrode head 17 contains a number of leg components 18 and 19 which are connected to the conductor 10 (not shown) in the electrode cable 4, and which serve as defibrillation surfaces. For clarity, only two leg components 18 and 19 are shown in FIGS. 3 and 4, however, the electrode head 17 can be provided with a large number of such leg components 18 and 19 evenly distributed on the distal end of the cable 4. The leg components 18 and 19 consist of a material, and have a shape so that they are in mechanical contact with each other, at least in part, in the passive position, as shown in FIG. 3. A separation element is disposed at the distal end of the electrode cable 4 between the leg components 18 and 19. This separation element can be an inflatable, balloon-like element 20, having an interior in communication with the pump 7 via the channel 12 in the electrode cable 4. Just before defibrillation, the balloon-like part 20 is inflated, in the same manner as described in conjunction with FIGS. 1 and 2, causing the leg components 18 and 19 to expand and to press against the surrounding heart wall. Defibrillation pulses are thereafter emitted. Because the balloon-like part 20 can be made relatively small, the pump 7 can be correspondingly small. After defibrillation, the electrode head 17 resumes its original passive position when the pump 7 evacuates the gas or liquid from the balloon-like element 20.

In a further version (not shown) of the defibrillation electrode 2, the movements of the leg components 18 and 19 can be controlled by a thin line or thread, connected through the channel 12 in the electrode cable 4, to a motorized spool contained in the defibrillator 1 from which the line or thread can be wound and unwound. The line and the motorized spool then replace the pump 7. When the line is tightened by winding onto the spool, the leg components 18 and 19 are pulled apart, and when the line is slackened by unwinding from the spool, the leg components 18 and 19 collapse in the configuration shown in FIG. 3.

Figure 5:
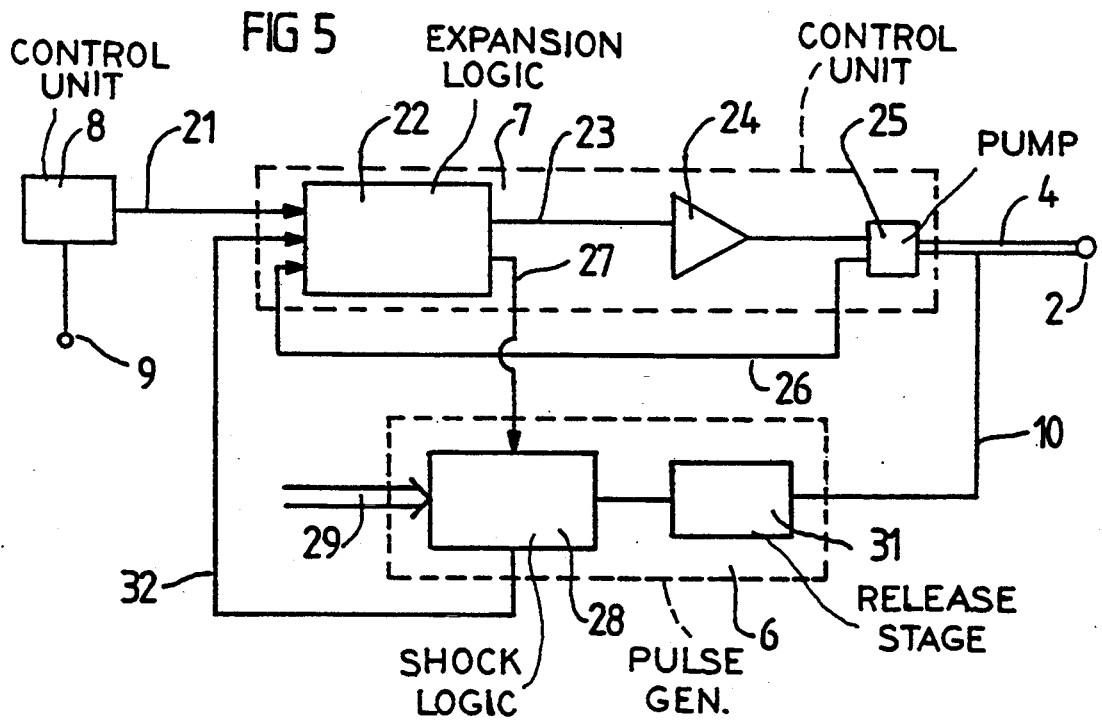
FIG. 5 is a block circuit diagram showing further details of the defibrillation system constructed in accordance with the principles of the present invention.

A block diagram of the defibrillation system is shown in FIG. 5. In the embodiment of FIG. 5, the sensor electrode 9 senses electrical heart signals. These signals are supplied to the control unit 8, which determines in a known manner whether cardiac fibrillation is present. If fibrillation is present and a defibrillation shock is to be emitted, a signal is supplied via a line 21 to the expansion logic 22, which is a part of the control unit 7. The output signal from the expansion logic 22 controls, via a line 23 and, if necessary, an amplifier 24, a pump 25 for expanding the electrode 2 via the electrode cable 4 in the described manner. Information regarding the status of the pump is relayed to the expansion logic 22 via a line 26. If the expansion logic 22 determines that the electrode head 2 has been expanded, a control pulse is sent via an output signal line 27 to the shock logic 28, which is a part of the pulse generator 6. Parameters such as the energy level, and others, can be programmed into the shock logic 28, such as by using an external programmer, as schematically indicated by the input line 29. The shock logic 28 generates an output signal which is supplied via a line 30 to a release stage 31, which enables the emission of a defibrillation pulse via the line 10 to the temporarily expanded electrode 2. The shock logic 28 also emits a signal which indicates when the shock has been emitted, this signal being delivered via a line 32 to the expansion logic 22. Upon receipt of this signal, the expansion logic 22 determines, depending on the signals from the control unit 8, whether the defibrillation pulse terminated the cardiac fibrillation, thereby causing the heart to resume normal activity, or whether fibrillation is still present, thus requiring the emission of an additional shock pulse. The head 14 of the electrode 2 is maintained in its expanded state if fibrillation has not been terminated. If fibrillation has been terminated, a signal is generated which, via the pump 25, restores the electrode head 14 to the non-expanded state, so that blood flow within the heart is not impeded.

Although modifications and changes may be suggested by those skilled in the art, it is the intention of the inventor to embody within the patent warranted hereon all changes and modifications as reasonably and properly come within the scope of his contribution to the art.

I claim as my invention:

1. A defibrillation system comprising:

stimulator means for generating defibrillation pulses;

at least two defibrillation electrodes connected to said stimulator means, at least one of said defibrillation electrodes being adapted for intracardiac placement;

said at least one defibrillation electrode adapted intracardiac placement including a flexible electrode cable having a proximal end connected to said stimulator means and a distal end having an electrode head with an expandable component carrying at least one defibrillation surface for delivering said defibrillation pulses to a heart;

means for expanding said expandable component from a non-expanded state wherein said electrode head does not impede blood flow to said heart, to an expanded state;

control means for sensing conditions indicative of a fibrillation episode of said heart and for supplying a control signal identifying a duration of said fibrillation episode to said stimulator means and to said means for expanding for causing said means for expanding to expand said expandable component of said electrode head from said non-expanded state to said expanded state for said duration of said fibrillation episode and for causing said stimulator means to generate said defibrillation pulses while said expandable component is in said expanded state.

2. A defibrillation system as claimed in claim 1 wherein said electrode head consists of substantially fluid-tight material.

3. A defibrillation system as claimed in claim 2 wherein said electrode head consists of elastic material.

4. A defibrillation system as claimed in claim 2 wherein said electrode head carries a plurality of filamentous conductors thereon forming said defibrillation surface, said filamentous conductors being arranged on said expandable component for permitting expansion of said expandable component.

5. A defibrillation system as claimed in claim 1 wherein said electrode head consists of at least two elongate, leg components forming said defibrillation surface, said leg components being attached at one end to said electrode cable and being in contact with each other, and wherein said expandable component is, disposed between said leg components, for causing said leg components to move toward and away from each other.

6. A defibrillation system as claimed in claim 5 wherein said expandable component comprises a substantially fluid-tight, balloon-like component connected to said electrode cable.

7. A defibrillation system as claimed in claim 6 wherein said electrode cable has a channel therein and wherein said means for expanding comprises pump means for pumping a fluid through said channel to said electrode head for inflating and deflating said balloon-like component.

8. A defibrillation system as claimed in claim 7 wherein said means for expanding comprises means for causing said balloon-like component to expand before enabling delivery of a defibrillation pulse.

9. A defibrillation system as claimed in claim 1 wherein said electrode head consists of elastic, substantially fluid-tight material, wherein said electrode cable has a channel therein, and wherein said means for expanding comprises pump means for delivering fluid to said electrode head for expanding said substantially fluid-tight material.

10. A defibrillation system as claimed in claim 1 wherein said control means comprises means for causing said means for expanding to expand said expandable component of said electrode head before enabling said stimulator means to generate said defibrillation pulses.

11. A method for defibrillating a heart comprising the steps of:

disposing at least one of a plurality of defibrillation electrodes in a ventricle of said heart;

providing said electrode disposed in said ventricle with an electrode head formed by substantially fluid-tight material and having an electrically conductive defibrillation surface thereon;

detecting conditions indicating the presence of cardiac fibrillation;

in the presence of cardiac fibrillation, expanding said electrode head by filling said electrode head with fluid to bring said electrode surfaces into contact with cardiac tissue; and delivering defibrillation pulses to a heart via said plurality of defibrillation electrodes.

* * * * *